(12) United States Patent
Kim et al.

(10) Patent No.: US 9,131,692 B2
(45) Date of Patent: Sep. 15, 2015

(54) ANTIBACTERIAL IMIDAZOLIUM COMPOUND AND ANTIBACTERIAL PHOTOCURABLE THIOL-ENE COMPOSITIONS COMPRISING THE SAME, AND ANTIBACTERIAL POLYMER COATINS PREPARED THEREFROM

(71) Applicant: Korea Institute of Science and Technology, Seoul (KR)

(72) Inventors: Man Ho Kim, Pyeongtaek (KR); Kwang Duk Ahn, Seoul (KR); Mirinae Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 13/768,373

(22) Filed: Feb. 15, 2013

(65) Prior Publication Data

US 2014/0212374 A1    Jul. 31, 2014

(30) Foreign Application Priority Data

Jan. 28, 2013    (KR) .................. 10-2013-0009528

(51) Int. Cl.
```
A01N 43/52      (2006.01)
A61K 8/72       (2006.01)
A01N 43/50      (2006.01)
C07D 233/58     (2006.01)
```

(52) U.S. Cl.
CPC .............. *A01N 43/50* (2013.01); *C07D 233/58* (2013.01)

(58) Field of Classification Search
None
See application file for complete search history.

(56) References Cited

U.S. PATENT DOCUMENTS

```
4,017,631  A  *   4/1977   Janssen et al. .............. 514/399
7,288,608  B2 *  10/2007   Bowman et al. ............. 525/535
2009/0270528 A1* 10/2009   Bowman et al. ............. 523/116
```

FOREIGN PATENT DOCUMENTS

```
KR      10-0752150        8/2007
KR    10-2010-0100809     9/2010
```

OTHER PUBLICATIONS

The Polymer Society of Korea, "Annual meeting of the Korean Ceramic Society", *Antibacterial Polymer Coatings by Photocuring of Imidazolium Salts*, Oct. 11-12, 2012, pp. 1-3.
Korean Office Action dated Jul. 1, 2014 in corresponding Korean Patent Application No. 10-2013-0009528.
"Antibacterial coatings on poly(fluoroethylenepropylene) films via grafting of 3-hexadecyl-1-vinylimidazolium bromide", Sisti et al., Progress in Organic Coatings, 73, 2012, pp. 257-263.
"Polymeric ionic liquids as selective coatings for the extraction of esters using solid-phase microextraction", Zhao et al., Journal of Chromatography A, 1208, 2008, pp. 1-9.

\* cited by examiner

*Primary Examiner* — Misook Yu
*Assistant Examiner* — Kauser M Akhoon
(74) *Attorney, Agent, or Firm* — Goldilocks Zone IP Law (57) ABSTRACT

An antibacterial imidazolium compound, a photocurable coating composition, and an antibacterial coating film includes a compound represented by Chemical Formula 1 shown below or derivatives thereof.

[Chemical Formula 1]

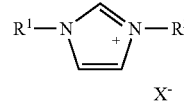

In Chemical Formula 1, description of $X^-$, $R^1$ and, $R^2$ is the same as in the detailed description of the invention. The antibacterial imidazolium compound has excellent antibiosis over various strains, and is included in a photocurable coating composition so as to provide an antibacterial coating film by a simple method. Also, in the antibacterial coating film, the antibacterial imidazolium compound is included as a monomer and chemically bonded to a polymer chain, and thus, antibacterial performance can be maintained for a long period of time.

4 Claims, 5 Drawing Sheets

FIG. 1

Photocured structure of antibacterial coating

FIG. 9

ANTIBACTERIAL IMIDAZOLIUM COMPOUND AND ANTIBACTERIAL PHOTOCURABLE THIOL-ENE COMPOSITIONS COMPRISING THE SAME, AND ANTIBACTERIAL POLYMER COATINS PREPARED THEREFROM

CROSS-REFERENCE TO RELATED APPLICATION

Pursuant to 35 U.S.C. §119(a), this application claims the benefit of earlier filing date and right of priority to Korean Application No. 10-2013-0009528, filed on Jan. 28, 2013, the contents of which is incorporated by reference herein in its entirety.

BACKGROUND OF THE INVENTION

1. Field of the Invention

The present disclosure relates to an antibacterial imidazolium compound with excellent antibacterial performance over various strains, a photocurable coating composition comprising the same, and an antibacterial polymer coating prepared therefrom. Particularly, the antibacterial polymer coating maintains antibacterial activity for a long period of time after preparing it in an environmentally-friendly manner.

2. Background of the Invention

As human beings come into contact with objects, they may be infected by various diseases. Contagious bacteria may be spread through direct contact with human beings, but in most cases, human beings are infected by contagious bacteria such as virus indirectly as they come into contact with surface of objects which has been contacted by other people.

As density of population is high and a floating population is large, people come into contact with objects more frequently. Surfaces of doors, buses, handles of subways, desks, vending machines, public toilets, and the like, people are in contact in daily lives serve as mediums of transmitting bacteria unless they are sterilized each time.

Besides commonly used objects, cell phones, computer keyboards, pens, telephones, or the like of individuals may cause microbism. Thus, the development of antibacterial material that may be applied to household items or objects commonly contacted by various people is required.

Bacteria have different cell characteristics (e.g., Gram positive *bacillus*, Gram negative *bacillus*, aerobic bacteria, anaerobic bacteria), and various cell shapes such as a spherical shape, a plate shape, a cylindrical shape, an aggregate thereof, and the like. Thus, a polymer of antibiosis is required to have a function of impeding growth of various bacteria, as well as a single particular virus or germ. Thus, an antibacterial polymer aims at exhibiting a physical, chemical mechanism such as damaging a cell membrane/cell wall or degenerate protein or respiratory inhibition, and the like. Also, in many cases, an antibacterial material with respect to a particular germ does not exhibit antibacterial function with respect to a cell having a different structure, so the development of an antibacterial polymer material having generality is far-off.

Various types of antibacterial compounds or materials having a low molecular weight have been developed and used as antibacterial materials in various materials. In order to easily apply antibacterial materials to articles or in terms of cost, a method of coating only a target surface is a method for economically providing antibiosis to surfaces of a product, while maintaining intrinsic properties (mechanical, physical, chemical qualities, etc.) of objects.

In the case of various existing antibacterial materials, in most cases, antimicrobials are physically mixed in a matrix polymer (resin) so as to be used (e.g., an antifungal paint used by mixing antimicrobial in paint).

In antibacterial materials including antimicrobials, antibacterial compounds having a low molecular weight are leached and discharged over time; so the antibacterial function of the surfaces of products are reduced over time. Also, existing antimicrobials are generally used as additives; so an excessive amount, rather than appropriate amount, is used, and only a portion of the antimicrobials in use are positioned on the surface of a material to exhibit antibacterial function. So antimicrobials in use are limitedly utilized. In products in which antimicrobials are physically mixed to be added, effective antibacterial ingredients are reduced due to continuous cleaning and exposure and antibacterial activity is rapidly reduced as a service life thereof elapses. Also, the leached antimicrobials are exposed to the surrounding environment to contaminate water, soil, and the like, of the nature, causing a serious problem in the environment.

Thus, research into an antibacterial polymer material preventing antimicrobials from being leached in spite of the long-term use by chemically binding monomers having an antibacterial function to polymer chains has been conducted [A. Munoz-Bonilla, Prog. Polym. Sci., 37, 281 (2012); S. Jiang, Z. Cao, Adv. Mater., 22, 920 (2010); F. Rubmer, et al., Macromolecules, 42, 8573 (2009); E.-R. Kenawy, et al, Biomacromolecules, 8, 1359 (2007); S. D. Worley, TRIP, 4, 364 (1996); T. Tashiro, Macromol. Mater. Eng., 286, 63 (2001)].

In an antibacterial polymer material including an antibacterial treating group which are bonded thereto, the antibacterial treating agent exists in a state of being directly bonded to a polymer chain, so antibiosis is maintained although it is cleaned. Thus, it has high applicability with respect to clothes, bedding, and medical fiber products.

However, since the antibacterial polymer known so far has insufficient antibacterial activity and is mostly in a water soluble ammonium salt state, it is insoluble in an organic solvent and thus its application is not easy. Also, a material is water soluble or bonded to a surface of a product through a post-crosslinking reaction, which is, thus, not appropriate to be used as a coating material. Thus, the development of a reactive antibacterial monomer and a polymer material, which has excellent antibacterial activity, is economical, and is environmentally-friendly photocurable, so as to be easily coated on surfaces of construction interior materials, various electronic devices, household items, apparel product, packing materials, and containers for food by using a photocurable reaction, is required.

SUMMARY OF THE INVENTION

Therefore, an aspect of the detailed description is to provide an antibacterial imidazolium compound having excellent antibacterial performance to various strains and a photocurable coating composition comprising the same. The coating composition may be coated on various products and photo-cured, to provide polymer coating capable of maintaining excellent antibiosis for a long period of time; being environmentally friendly and stably prepared without using a toxic organic solvent, and providing antibacterial polymer coating having excellent strength.

To achieve these and other advantages and in accordance with the purpose of this specification, as embodied and broadly described herein, an antibacterial imidazolium compound is represented by Chemical Formula 1 shown below:

[Chemical Formula 1]

In Chemical Formula 1, $X^-$ is an anion selected from the group consisting of $Cl^-$, $Br^-$, $BF_4^-$, $PF_6^-$, $SbF_6^-$, $CF_3SO_3^-$, $(CF_3SO_3)_2N^-$, $ArSO_3^-$, $CF_3CO_2^-$, and $CH_3CO_2^-$, $R^1$ is a functional group including carbon-carbon double bond, and $R^2$ is an alkyl group represented by $(CH_2)_xY$. In $(CH_2)_xY$, x is an integer of 7 to 20 and Y is H, OH, or $CO_2H$.

A photocurable coating composition according to another embodiment of the present invention comprises 1 to 50 mol % of the antibacterial imidazolium compound, 20 to 50 mol % of a thiol compound including 1 to 4 thiol groups, 20 to 50 mol % of ene compound including double bonds, and 0.1 to 10 mol % of photo initiator.

An antibacterial polymer coating according to another embodiment of the present invention comprises sulfur-carbon bonds included in a polymer coating by photocuring the photocurable coating composition, and the polymer includes a repetitive unit represented by Chemical Formula 2-1 or 2-2 shown below.

[Chemical Formula 2-1]

[Chemical Formula 2-2]

In Chemical Formulas 2-1 and 2-2, A is a functional group derived from a thiol compound including three or more thiol groups, B is a functional group derived from an ene compound including two or more carbon-carbon double bonds, and Im is a functional group derived from an antibacterial imidazolium compound. In Chemical Formulas 2-1 and 2-2, "c" is carbon derived from the ene compound and "s" is sulfur derived from a thiol group.

A method for preparing an antibacterial imidazolium compound according to another embodiment of the present invention comprises: preparing an antibacterial imidazolium compound represented by Chemical Formula 1 by reacting a compound represented by Chemical Formula 3 and a compound represented by Chemical Formula 4.

[Chemical Formula 3]

[Chemical Formula 4]

In Chemical Formulas 3 and 4, $X^-$ is an anion selected from the group consisting of $Cl^-$, $Br^-$, $BF_4^-$, $SbF_6^-$, $CF_3SO_3^-$, $(CF_3SO_3)_2N^-$, $ArSO_3^-$, $CF_3CO_2^-$, and $CH_3CO_2^-$, $R^1$ and $R^2$ are selected from a functional group including a carbon-carbon double bond and an alkyl group represented by $(CH_2)_xY$, alternatively. In $(CH_2)_xY$, x is an integer of 7 to 20 and Y is H, OH, or $CO_2H$.

Hereinafter, embodiments of the present invention will be described.

In an embodiment of the present invention, selecting alternatively means that if any one is selected alternatively from two items, the selected one cannot be selected again. For example, selecting B1 and B2 by A1 and A2 refers to that if A1 selects B1, A2 selects B2 and B1 cannot be selected by A2, and if A1 selects B2, A2 selects B1.

An antibacterial imidazolium compound according to an embodiment of the present invention includes a compound represented by Chemical Formula 1 shown below.

[Chemical Formula 1]

In Chemical Formula 1, $X^-$ is an anion selected from the group consisting of $Cl^-$, $Br^-$, $BF_4^-$, $PF_6^-$, $CF_3SO_3^-$, $(CF_3SO_3)_2N^-$, $ArSO_3^-$, $CF_3CO_2^-$, and $CH_3CO_2^-$. $R^1$ is a functional group including a carbon-carbon double bond and the carbon-carbon double bond may be included in the end of the function group. $R^2$ is an alkyl group represented by $(CH_2)_x$Y. In $(CH_2)_xY$, x is an integer of 7 to 20, preferably, an integer of 10 to 20 and more preferably, an integer of 12 to 20. Y is H, OH, or $CO_2H$.

The imidazolium salt compound represented by Chemical Formula 1 may serve as a monomer capable of forming a polymer coating thin film, while maximizing an antibacterial activity; by introducing a carbon-carbon double bond group to imidazolium salt having antibacterial activity with respect to various microorganisms and changing a number of carbons of a substituted alkyl group.

Namely, it is a compound obtained by synthesizing a carbon-carbon double bond, which is additionally reactive, so as to be included in an imidazolium salt compound having excellent antibacterial function, which is utilized as a monomer of a polymer coating thin film.

$R^1$ is a chain functional group as one selected from the group consisting of Chemical Formula 1-1 to Chemical Formula 1-5 or a ring functional group of Chemical Formula 1-6.

$-(CH_2)_a-CH=CH_2$   [Chemical Formula 1-1]

$-(CH_2)_a-O-CH=CH_2$   [Chemical Formula 1-2]

$-(CH_2)_a-O-CH=CH-CH_3$   [Chemical Formula 1-3]

$-(CH_2)_a-O-(CH_2)_b-CH=CH_2$   [Chemical Formula 1-4]

$-(CH_2)_a-(CH=CH)_2-H$   [Chemical Formula 1-5]

[Chemical Formula 1-6]

In Chemical Formulas 1-1 to 1-5, a is an integer of 0 to 5, independently; and in Chemical Formula 1-4, b is an integer of 0 to 5.

The antibacterial imidazolium compound may include any one selected from the group consisting of 1-allyl-3-dodecylimidazolium salt, 1-dodecyl-3-4-vinylbenzylimidazolium salt, and a combination thereof.

The antibacterial imidazolium compound may be a liquid having viscosity ranging from 50 to 3000 cPs at a temperature of 25° C. Within the range of viscosity, an antibacterial polymer coating thin film may be formed without using an additional organic solvent or by minimizing the use of an organic solvent.

In preparing a thiol-ene photocurable composition for providing an antibacterial polymer coating thin film, a coating composition may be prepared by mixing antibacterial imidazolium compounds without using a solvent. In general, an organic solvent is used in forming a polymer thin film, which is harmful to human body and the environment, but in the case of using the antibacterial imidazolium compound according to an embodiment of the present invention as an antibacterial monomer, the thiol-ene photocurable composition is a liquid, eliminating the use of an organic solvent, and thus, an antibacterial coating film can be provided in an environmentally friendly and stable manner.

The antibacterial imidazolium compound according to an embodiment of the present invention provides imidazolium salt which has a low degree of harm to ecosystems and has antibacterial activity with respect to extensive harmful microorganisms, and may be utilized as an antibacterial monomer allowing for a formation of an antibacterial coating thin film by a photocurable coating technology without using an organic solvent. Also, the imidazolium compound acts as a mechanism which attracts microorganisms to the compound and makes membranes of microorganisms to be damaged by an alkyl group of the compound, having excellent antibacterial activity.

The method for preparing an antibacterial imidazolium compound according to another embodiment of the present invention provides an antibacterial imidazolium compound represented by Chemical Formula 1 by reacting a compound represented by Chemical Formula 3 shown below and a compound represented by Chemical Formula 4.

[Chemical Formula 3]

$R^1 - N \diagup\diagdown N$

[Chemical Formula 4]

$X - R^2$

[Chemical Formula 1]

$R^1 - N \diagup\diagdown \overset{+}{N} - R^2 \quad X^-$

In Chemical Formulas 3, 4, and 1, $X^-$ is an anion selected from the group consisting of $Cl^-$, $Br^-$, $BF_4^-$, $PF_6^-$, $SbF_6^-$, $CF_3SO_3^-$, $(CF_3SO_3)_2N^-$, $ArSO_3^-$, $CF_3CO_2^-$, and $CH_3CO_2^-$. $R^1$ and $R^2$ are selected from a functional group including a carbon-carbon double bond and an alkyl group represented by $(CH_2)_xY$, alternatively. In $(CH_2)_xY$, x is an integer of 7 to 20, and preferably, an integer of 10 to 20, and more preferably, an integer of 12 to 20. Y is H, OH, or $CO_2H$.

The foregoing reaction may include a process of obtaining an antibacterial imidazolium compound represented by Chemical Formula 1 by mixing the compound, which is dissolved in a solvent, represented by Chemical Formula 3 with the compound represented by Chemical Formula 4, and reacting the mixture at a temperature ranging from 60 to 70° C. for 12 to 14 hours, and the process may be represented by Reaction Formula 1 shown below.

[Reaction Formula 1]

In Reaction Formula 1, a description of $R^1$, $R^2$, and $X^-$ is the same as that of Chemical Formulas 3, 4, and 1; so it is omitted herein. However, in Reaction Formula 1, $X^-$ may be a halogen element and may be substituted by any one selected from the group consisting of $BF_4^-$, $PF_6^-$, $SbF_6^-$, $CF_3SO_3^-$, $(CF_3SO_3)_2N^-$, $ArSO_3^-$, $CF_3CO_2^-$, and $CH_3CO_2^-$; in a follow-up reaction in addition to the reaction of Reaction Formula 1.

A photocurable coating composition according to another embodiment of the present invention includes the antibacterial imidazolium compound as a monomer included in a polymer coating film.

The photocurable coating composition includes 1 to 50 mol % of antibacterial imidazolium compound according to an embodiment of the present invention, 20 to 50 mol % of thiol compound including one to four thiol groups, 20 to 50 mol % of ene compound including a carbon double bond (—C=C—), and 0.1 to 10 mol % of photoinitiator. The antibacterial imidazolium compound, the thiol compound, and the ene compound may constitute a polymer chain included in a coating film with a curing reaction.

The photocurable coating composition may include 5 to 30 mol % of antibacterial imidazolium compound, 20 to 50 mol % of thiol compound including one to four thiol groups, 20 to 50 mol % of ene compound including a carbon double bond, and 0.1 to 10 mol % of photoinitiator. The photocurable coating composition may include 10 to 20 mol % of antibacterial imidazolium compound, 28 to 48 mol % of thiol compound including one to four thiol groups, 27 to 48 mol % of ene compound including a carbon double bond, and 0.1 to 10 mol % of photoinitiator.

The photocurable coating composition may include 5 mol % or more of antibacterial imidazolium compound, and may include 10 mol % of more of antibacterial imidazolium compound. In such a case, the photocurable coating composition may exhibit excellent antibacterial activity with respect to Gram positive *bacillus* as well as Gram negative *bacillus*.

The antibacterial imidazolium compound according to an embodiment of the present invention is the same as described above, so a description thereof will be omitted.

The thiol group included in the thiol compound may be reacted with the carbon-carbon double bond (—C=C—) included in the antibacterial imidazolium compound and the ene compound by UV light irradiation or e-beam irradiation to generate a sulfur-carbon bond.

The thiol compound may be a multi-thiol compound including two or more thiol groups, and preferably, the thiol compound may be a multi-thiol compound including three or more thiol group in the compound.

The thiol compound may be any one selected from the group consisting of alkane dithiol, {trimethylolpropane tris(3-mercaptopropionate)}, {trimethylolpropane tris(2-mercaptobutyrate)}, {buthanediol bis(3-mercaptopropionate)}, {butanediol bis(2-mercaptobutyrate)}, {pentaerythritol tetrakis(3-mercaptopropionate)}, {pentaerythritol tetrakis(2-mercaptobutyrate)}, {1,3,5-tri(2-hydroxyethyl)-1,3,5-triazine-2,4,6-trione tris(3-mercaptopropionate)}, {1,3,5-tri(2-hydroxyethyl)-1,3,5-triazine-2,4,6-trione tris(2-mercaptobutyrate)}, and a combination thereof.

The ene compound may be a compound in which a carbon-carbon double bond exists, and a multi-ene compound including two or more double bonds may be applied. The ene compound may serve as a monomer constituting a polymer and also serve as a diluent for adjusting viscosity of the photocurable coating composition such that the photocurable coating composition can be appropriately coated on a product.

The ene compound may be any one selected from the group consisting of allyl ether, allyl amine, vinyl ether, (meta) acrylate, unsaturated ester, styrene, maleimide, norbornene, and a combination thereof.

The ene compound may include any one selected from the group consisting of pentaerythritol triallyl ether, triallyloxy triazine, triallyl isocyanurate, alkane divinyl ether, trimethylolpropane triallyl ether, {multi(dimethylsiloxane)dinorbornene}, and a combination thereof.

A photoinitiator may be any one which can induce a sulfur-carbon bond between thiol and carbon-carbon double bond. In detail, it may serve to induce a radical to be generated from the photoinitiator according to UV light irradiation or e-beam irradiation to extract hydrogen from a thiol group to generate a sulfur radical, and allow the sulfur radical to be added to a carbon-carbon double bond to generate a new sulfur-carbon bond. The photocurable coating composition may further include a photosensitizer, a pigment, a filler, and the like, as necessary.

The photocurable coating composition may be a liquid having viscosity ranging from 50 to 3000 cPs at a temperature of 25° C. The photocurable coating composition may form a coating film according to a simple, environmentally friendly method such as photocuring or e-beam curing, and may include antibacterial imidazolium compound as a monomer in a polymer chain or directly connected thereto to provide a long-term antibacterial activity. In addition, since the used monomers have little bad smell, having advantages in the process of preparing the coating composition and forming the coating film is not harmful and storage stability is excellent.

An antibacterial coating film according to another embodiment of the present invention includes an antibacterial imidazolium monomer, and the polymer may include a repetitive unit represented by Chemical Formula 2-1 or 2-2.

[Chemical Formula 2-1]

[Chemical Formula 2-2]

In Chemical Formula 2-1 and 2-2, A is a functional group derived from a thiol compound including three or more thiol groups, B is a functional group derived from an ene compound including two or more carbon-carbon double bonds, and Im is a functional group derived from an antibacterial imidazolium compound. In Chemical Formulas 2-1 and 2-2, c is carbon derived from the ene compound and s is sulfur derived from a thiol group.

Figure 1:
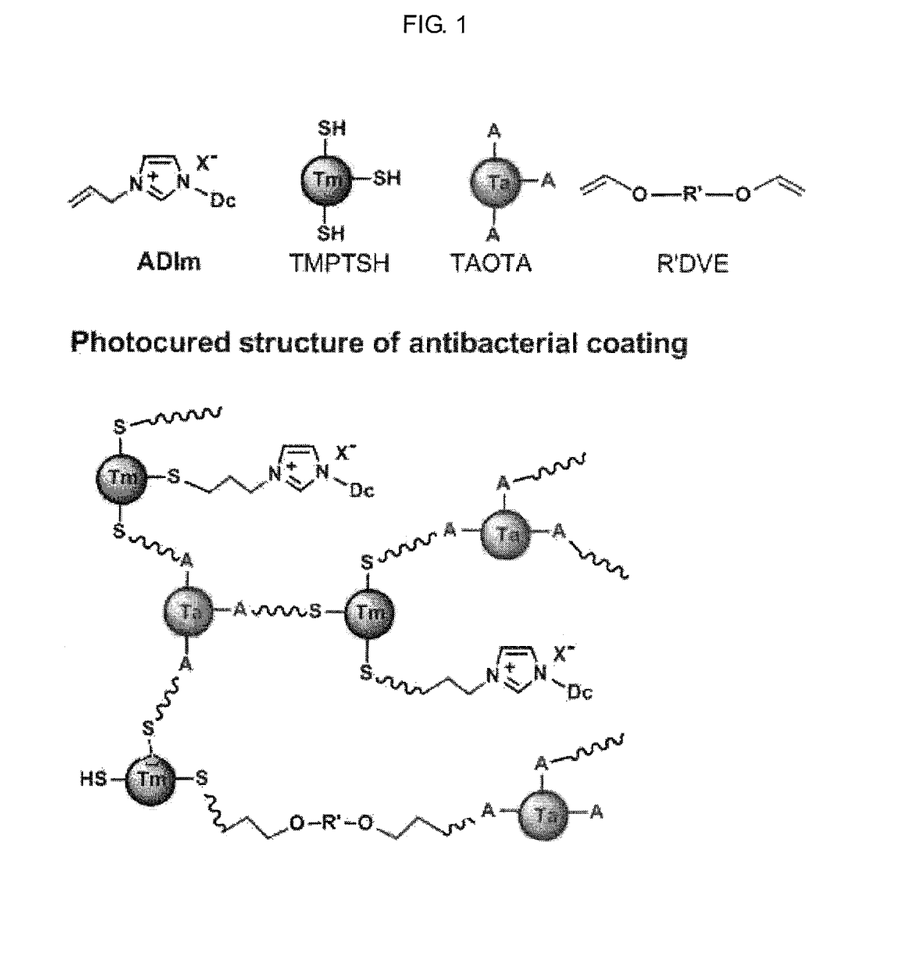
FIG. 1 is a view illustrating a structure of a polymer included in an antibacterial coating film.

A structure of a polymer included in the antibacterial coating film is illustrated in FIG. 1. Referring to FIG. 1, it shows an example in which TMPTSH is used as a thiol compound and TAOTA is used as an ene compound. The thiol compound and the ene compound illustrated in FIG. 1 are represented by Chemical Formula 2-3.

[Chemical Formula 2-3]

As illustrated in FIG. 1, a high-strength antibacterial polymer coating according to an embodiment of the present invention may be obtained by including a repetitive unit represented by Chemical Formulas 2-1 and/or 2-2. Also, since the antibacterial imidazolium monomer represented by Chemical Formula 1 is directly connected to the polymer chain, antibacterial activity can be maintained for a long period of time, a leakage of an antibacterial material to an ecosystem is minimized, and a generation of tolerance with respect to an antibacterial effect can be minimized.

This effect is differentiated from the case of forming a thin film by physically mixing antibacterial components, such that leaching of antibacterial compound is minimized during a usage process. An occurrence of a phenomenon in which antibacterial activity of the coating film is rapidly reduced with the passage of time is prevented and a waste of an antibacterial imidazolium compound is prevented.

Also, since a photocuring and e-beamcuring reaction between the thiol compound and the ene compound is used to make surface coating, the coating film can be easily formed and the antibacterial coating film can be formed within a short time through a simple process of irradiating UV light having a short wavelength of about 400 nm or lower or electron beams. The simple photocuring technique is an energy saving method which can be easily applied to automation facilities and provides an antibacterial coating in an economical manner.

In addition, the antibacterial photocuring process may not require or minimize the use of an additional organic solvent, and thus, it can provide an environmentally friendly antibacterial coating that does not discharge a volatile organic compound harmful to the environment.

The coating film may include 5~10 mol % of more of antibacterial imidazolium compounds, and in this case, more excellent antibacterial activity can be obtained.

In thiol-ene photocuring, the antibacterial coating includes sulfur-carbon bonds generated in the process of photoreaction and cross-linking concurrently occur, a curing reaction is fast and effective, and since insolubilization sue to curing is sufficiently performed, a transparent and smooth antibacterial coating film can be provided The antibacterial coating film can be formed without using a toxic solvent such as a volatile organic solvent, is environmentally friendly, and can be simply formed through a photocuring process. It can have long-term antibacterial activity.

The antibacterial coating film can be advantageously used as an antibacterial coating on surfaces of objects such as various daily household items, cell phones, handles, various living, construction interior materials, public health hygiene items, hospital supplies, public equipment, and the like. Also, the antibacterial coating film may be easily coated on construction materials of offices, hospitals, and interior materials of vending machines, public telephones, toilet, subway, buses, and the like; used by the public to provide products with antibiosis and may also be used as an environmentally friendly antibacterial polymer coating material in housing exterior materials coating of electric/electronic products, packing materials, materials for foods and storage, etc.

The antibacterial imidazolium compound, the photocurable coating composition including the antibacterial imidazolium compound, and the coating film provide the antibacterial imidazolium compound having excellent antibacterial performance on various strains and a coating composition capable of quickly forming a coating film through a photocuring method by including the antibacterial imidazolium compound. The coating film formed to include the antibacterial imidazolium compound and the coating composition can be quickly and simply coated on a surface of a product through thiol-ene curing, and has excellent antibiosis so as to be applied for various products. Also, since a toxic organic solvent is not used, the coating film can be safely used in materials including food packing materials and an environmentally friendly coating film can be formed.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Hereinafter, examples will be described in detail with reference to the accompanying drawings such that they can be easily practiced by those skilled in the art to which the present invention pertains. The invention may, however, be embodied in many different forms and should not be construed as being limited to the examples set forth herein.

1. Synthesis of Antibacterial Imidazolium Compound and Thion-ene Photocuring

EXAMPLE 1

Synthesis of 1-allyl-3-dodecyl Imidazolium Salt [ADIm(Br)]

Allyl group-substituted N-allylimidazole (Aim) and 12-bromododecyl was reacted to prepare 1-allyl 3-dodecylimidazolium bromide salt compound [ADIm(Br)] substituted with an alkyl group including 12 carbons as follows.

10.34 g (0.092 mol) of 1-allylimidazole was dissolved in 20 ml of dimethylsulfoxide (DMSO), 27.64 g (0.111 mol) of 1-bromododecane was put therein, and stirred for reaction at a temperature of 60° C. for 12 hours. After the reaction was terminated, a solvent was distilled under reduced pressure, and the residue was precipitated in an excess amount of diethylether to obtain 18.78 g (yield, 57%) of allyldodecylimidazolium salt as a yellow liquid having low viscosity (X is a bromine ion).

$^1$H NMR (CDCl$_3$, 200 MHz) 10.4 (s, 1H), 7.4~7.6 (m, 2H), 5.8~6.2 (m, 1H), 5.2~6.2 (d, 1H), 5.2~5.6 (s, 2H), 4.9~5.1 (d, 2H), 4.2~4.4 (t, 2H), 1.7~2.0 (m, 2H), 1.0~1.4 (m, 18H), 0.7~0.9 (t, 3H).

[Reaction Formula 2]

Aim

-continued

ADIm (Br)

EXAMPLE 2

Evaluation of Thiol-ene Photocuring Speed of 1-allyl-3-dodecyl Imidazolium Salt [ADIm(Br)]

A thiol-ene photocurable composition was prepared by using the antibacterial imidazolium salt monomer synthesized in Example 1 and a photocurable reaction thereof was evaluated.

1 molar ratio of imizolium ADIm(Br) prepared in Example 1, 2 molar ratio of trimethylolpropane tris(3-mercaptopropyonate) as a crosslinker, 2 molar ratio of 2,4,6-triallyloxy-1,3,5-triazine, and 0.05 molar ratio of 1-hydroxycyclohexylphenylketone as a photoinitiator was properly mixed to prepare a photocurable composition.

10 mg of the prepared photocurable composition containing about 20 mol % of ADIm was taken, and a heat flow of photocuring reaction as measured by using differential photocalorimeter (DPC) was used to compare and evaluate photocuring reaction speeds. For the photocuring reaction evaluation equipment, a DPC combined with Model DSC 2910 of TA instruments Co. including an 250 W mercury lamp was used.

According to results obtained by measuring the photocuring reaction speeds by using DPC, a heating flow of Example 2 was 6.0 W/g at the maximum in the photocuring reaction, and the photocuring time was less than 1 minute, which was evaluated to be sufficiently fast.

EXAMPLES 2-1 to 2-5

Evaluation of Photocuring Speed of Antibacterial Coating Using UV Conveyer Belt

In order to test film formation capability in case of being applied as a coating film to an actual product, a photocuring reaction speed in the event of exposure, and the like, was measured in the same manner as that of Example 2 by using a UV conveyer stepper and analyzed.

Ingredients with compositions of Examples 2-1 to 2-5 are shown in Table 1. Respective compositions having viscosity were applied to a glass plate or a polyester film while changing the content of antibacterial monomers, and light was irradiated at a conveyer speed of 5 m/min by using a 40 mw/cm$^2$ UV conveyer stepper.

As shown in Table 1, photocurable compositions containing 10, 5, 1, 0.1 mol % of antibacterial imidazolium salt (ADIm) were prepared and photocuring reaction thereof was evaluated. As a result, the surface was smoothly and solidly cured to form films having a thickness of 0.03 mm of Examples 2-1 to 2-5, and thus, it was confirmed that formation of transparent photocurable polymer films were formed. It was also confirmed that as the content of antibacterial imidazolium salt (ADIm) was reduced, a photocuring time in the conveyer belt was less than 30 seconds, which is sufficiently fast.

TABLE 1

| compositions and heating value | Example 2-1 | Example 2-2 | Example 2-3 | Example 2-4 | Example 2-5 |
| --- | --- | --- | --- | --- | --- |
| 1-allyl-3-dodecylimidazolium salt [ADIm(Br)] [mole] | 1 | 1 | 0.5 | 0.1 | 0.01 |
| Trimethylolpropane tris(3-mercaptopropyonate) [TMPTSH] [mole] | 2 | 4.5 | 4.75 | 4.95 | 5 |
| 2,4,6-triallyloxy-1,3,5-triazine [TAOTA] [mole] | 2 | 4.5 | 4.75 | 4.95 | 5 |
| 1-hydroxycyclohexylphenylketone [photoinitiator] [mole] | 0.05 | 0.05 | 0.05 | 0.05 | 0.05 |
| Content of antibacterial compound [mole %] | about 20 | about 10 | about 5 | about 1 | about 0.1 |
| heating value [W/g] | 6 | 6 | 10 | 19 | 25 |

EXAMPLE 3

Thiol-ene Photocuring of 1-dodecyl-3-(4-vinylbenzyl)imidazolium Salt

The following thiol-ene photocurable composition was prepared by using 1-dodecyl-3-(4-vinylbenzyl)imidazolium salt (chlorine ion))[DStIm(Cl)] as antibacterial imidazolium salt, and the photocuring reaction thereof was evaluated.

1 molar ratio of 1-dodecyl-3-(4-vinylbenzyl)imidazolium salt, 2 molar ratio of trimethylolpropane tris(3-mercaptopropyonate) as a crosslinker, 2 molar ratio of 2,4,6-triallyloxy-1,3,5-triazine, and 0.05 molar ratio of 1-hydroxycyclohexylphenylketone as a photoinitiator were properly mixed to prepare a photocurable composition and 10 mg of the composition was taken to measure a photocuring reaction speed by using DPC. The photocuring reaction speed of the antibacterial photocurable composition containing the antibacterial dodecylvinylbenzylimidazolium salt measured by the DPC was less than 1 minute, which was evaluated to be sufficiently fast.

EXAMPLES 3-1 to 3-5

Evaluation of Photocuring Speed of Antibacterial Coating Using UV Conveyer Belt

In order to check actual film formation capability, photocurable composition samples (Examples 3-1 to 3-5, please refer to Table 2 for composition ratios of respective samples) having viscosity were applied to a glass plate or a polyester film and light was irradiated at a conveyer speed of 5 m/min by using a 40 mw/cm$^2$ UV conveyer belt. As a result, the surface was smoothly and solidly cured to form films having a thickness of 0.03 mm, and it was confirmed that formation of transparent photocurable polymer films were formed.

to form transparent smooth photocurable films (having a thickness of about 0.03 mm) within less than 1 minute.

TABLE 2

| compositions | Example 3-1 | Example 3-2 | Example 3-3 | Example 3-4 | Example 3-5 |
|---|---|---|---|---|---|
| 1-dodecyl-3-(4-vinylbenzyl)imidazolium salt [DStIm(Cl)] [mole] | 1 | 1 | 0.5 | 0.1 | 0.01 |
| Trimethylolpropane tris(3-mercaptopropyonate) [TMPTSH] [mole] | 2 | 4.5 | 4.75 | 4.95 | 5 |
| 2,4,6-triallyloxy-1,3,5-triazine [TAOTA] [mole] | 2 | 4.5 | 4.75 | 4.95 | 5 |
| 1-hydroxycyclohexylphenylketone [photoinitiator] [mole] | 0.05 | 0.05 | 0.05 | 0.05 | 0.05 |
| Content of antibacterial compound [mole %] | About 20 | About 10 | About 5 | About 1 | About 0.1 |

EXAMPLES 4-1 to 4-9

Thiol-ene Photocuring of Imidazolium Salt and Acrylate

Photocurable compositions like the compositions of Table 3 were prepared while changing the content by using antibacterial imidazolium salt and various acrylic acid esters, and then the thiol-ene photocuring reaction was evaluated. The photocurable compositions were mixed, coated, and UV light was irradiated thereto. A transparent, smooth photocurable film having a thickness of about 0.03 mm was formed within less than 30 seconds.

TABLE 3

| compositions | Example 4-1 | Example 4-2 | Example 4-3 | Example 4-4 | Example 4-5 | Example 4-6 | Example 4-7 | Example 4-8 | Example 4-9 |
|---|---|---|---|---|---|---|---|---|---|
| ADIm(Br) [1)] [mole] | 1 | 1 | 1 | 3 | 3 | 1 | 1 | — | — |
| DStIm(Cl) [2)] [mole] | — | — | — | — | — | — | — | 1 | 1 |
| TMPTSH [3)] [mole] | 1 | 1 | — | 1 | 1 | 1 | 1 | 1 | 1 |
| TMPTA [4)] [mole] | — | — | 1 | — | 1 | 1 | 1 | — | — |
| HDDA [5)] [mole] | 1 | 3 | 3 | 3 | 1 | 1 | 2 | 1 | 3 |
| photoinitiator [6)] [mole] | 0.05 | 0.05 | 0.05 | 0.05 | 0.05 | 0.05 | 0.05 | 0.05 | 0.05 |
| Content of antibacterial compound [mole %] | About 33 | About 20 | About 20 | About 43 | About 50 | About 25 | About 20 | About 33 | About 20 |

[1)] 1-allyl-3-dodecylimidazolium salt
[2)] 1-dodecyl-3-(4-vinylbenzyl)imidazolium salt
[3)] Trimethylolpropane tris(3-mercaptopropyonate)
[4)] Trimethylolpropane triacrylate
[5)] 1,6-hexanediol diacrylate
[6)] 1-hydroxycyclohexylphenylketone

EXAMPLES 5-1 to 5-6

Thiol-Ene Photocuring of Imidazolium Salt and 1,4-butanediol Divinyl Ether

Photocurable compositions (Examples 5-1 to 5-4) of 1-allyl-3-dodecylimidazolium salt, 1,4-butanediol divinyl ether, and photocurable compositions (Examples 5-5 and 5-6) of 1-dodecyl-3-(4-vinylbenzyl)imidazolium salt were prepared by the content of Table 4 and thiol-ene photocuring reaction was evaluated.

The photocurable compositions of Examples 5-1 to 5-6 were mixed, respectively, and UV light was irradiated thereto

TABLE 4

| Composition | Example 5-1 | Example 5-2 | Example 5-3 | Example 5-4 | Example 5-5 | Example 5-6 |
|---|---|---|---|---|---|---|
| 1-allyl-3-dodecylimidazolium salt [ADIm(Br) [mol] | 1 | 1 | 1 | 1 | — | — |
| 1-dodecyl-3-(4-vnylbenzyl)imidazolium salt [DstIm(Cl) [mol] | — | — | — | — | 1 | 1 |

TABLE 4-continued

| Composition | Example 5-1 | Example 5-2 | Example 5-3 | Example 5-4 | Example 5-5 | Example 5-6 |
|---|---|---|---|---|---|---|
| Trimethylolpropane tris (3-mercaptopropyonate) [TMPTSH] [mol] | 1 | 1 | 2 | 2 | 2 | 2 |
| 1,4-butanediol divinylether [DBVE] [mol] | 1 | 3 | 3 | 6 | 3 | 6 |
| 1-hydroxycyclohexylphenylketone [photoinitiator] [mol] | 0.05 | 0.05 | 0.05 | 0.05 | 0.05 | 0.05 |
| Content of antibacterial component [mol %] | About 33 | About 20 | About 17 | About 11 | About 17 | About 11 |

EXAMPLES 6-1 to 6-3

Thiol-ene Photocuring of Antibacterial Imidazolium Salt, Acrylate, and 1,4-butanediol Divinyl Ether Photocurable compositions of 1-allyl-3-dodecylimidazolium salt, acrylate, and 1,4-butanediol divinyl ether were prepared by the contents of Table 5 and thiol-ene photocuring reaction was evaluated.

The photocurable compositions were mixed under the following conditions and UV light was irradiated thereto to form transparent smooth photocuring films (having a thickness of about 0.03 mm) within less than 1 minute.

TABLE 5

| Composition | Example 6-1 | Example 6-2 | Example 6-3 |
|---|---|---|---|
| 1-allyl-3-dodecylimidazolium salt [ADIm(Br)] [mol] | 1 | 1 | 1 |
| Trimethylolpropane tris (3-mercaptopropyonate) [TMPTSH] [mol] | 2 | 1 | 1 |
| Trimethylolpropane triacrylate [TMPTA] [mol] | — | 1 | 1 |
| 1,4-butanediol divinylether [DBVE] [mol] | 3 | 3 | 3 |
| 1,6-hexandiol diacrylate [HDDA] [mol] | 2 | 2 | 2 |
| 1-hydroxycyclohexylphenylketone [photoinitiator] [mol] | 0.05 | 0.05 | 0.05 |
| Content of antibacterial component [mol %] | About 12.5 | About 12.5 | About 11 |

2. Evaluation of Antibacterial Performance of Photocured Polymer Film

EXAMPLE 7

Test of Antibacterial Activity of Photocurable Polymer Film According to Concentration of Imidazolium Salt (1) Preparation of Strain and Culture Medium In order to test and evaluate an antibacterial activity of imidazolium salt to and photocured film prepared in the example, staphylococcus [Staphylococcus aureus (ATCC 65389)] as Gram positive bacillus and colon bacterium [Escherichia coli (ATCC 10536)] as Gram negative bacillus were used as representative bacteria of a life environment. Nutrient agar was used and each strain was cultivated in an incubator for 24 hours at 37° C. A formed colony was inoculated to nutrient broth and cultivated in a shaking incubator at 37° C. for 24 hours. The culture medium of each bacterium was applied according to parallel streak method (AATCC TM147) and used to test antibacterial activity evaluation.

(2) Evaluation of Antibacterial Activity of Samples According to Imidazolium Content and Results Thereof In order to evaluate antibacterial activity of a film sample containing ADIm(Br) and DStIm(Cl) as two types of imidazolium salt, test was performed as follows.

A composition including an imidazolium compound was coated on a slide glass plate, and the photocured antibacterial polymer coating was sterilized at 121° C. for 15 minutes in a high pressure sterilizer. Staphylococcus or colon bacterium culture medium were streaked on a Mueller-Hinton Agar (MHA) in a petri dish, on which the slide glass plate coated with different types of photocured samples was placed.

After the MHA culture medium was cultivated in an incubator at 37° C. for 24 hours, and growth of bacteria in the vicinity of the sample glass plate was observed and the results of the antibacterial results are shown in Table 6 below.

TABLE 6

Evaluation of antibacterial activity

Figure 2:
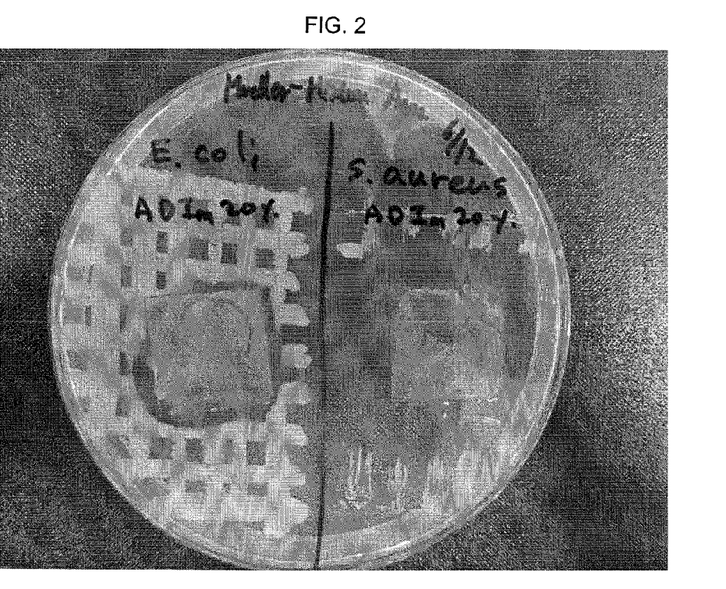
FIG. 2 is a photograph of antibacterial activity evaluation according to example 2-1.
Figure 3:
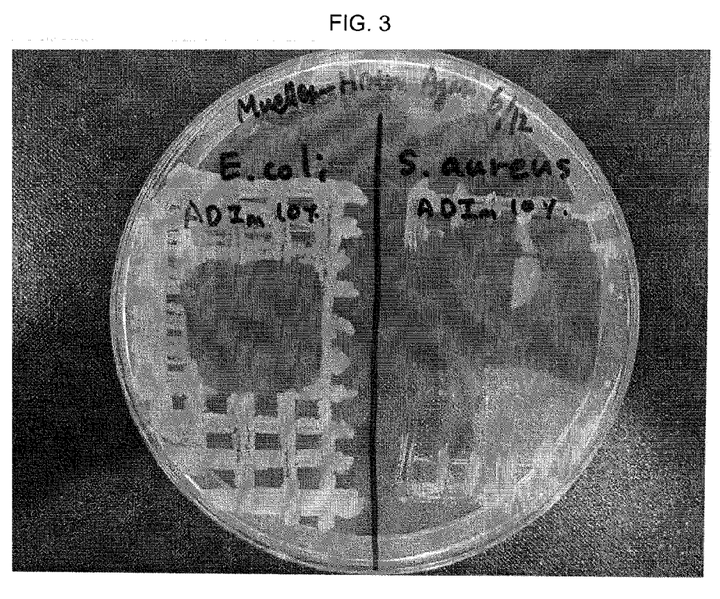
FIG. 3 is a photograph of antibacterial activity evaluation according to example 2-2.
Figure 4:
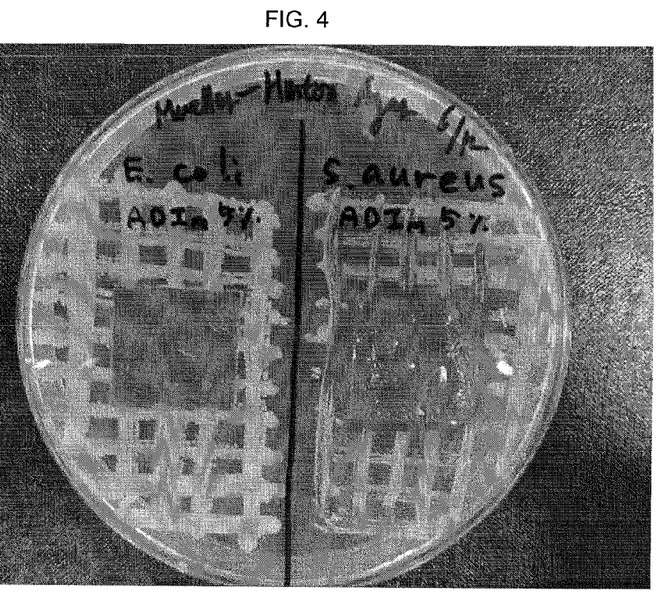
FIG. 4 is a photograph of antibacterial activity evaluation according to example 2-3.
Figure 5:
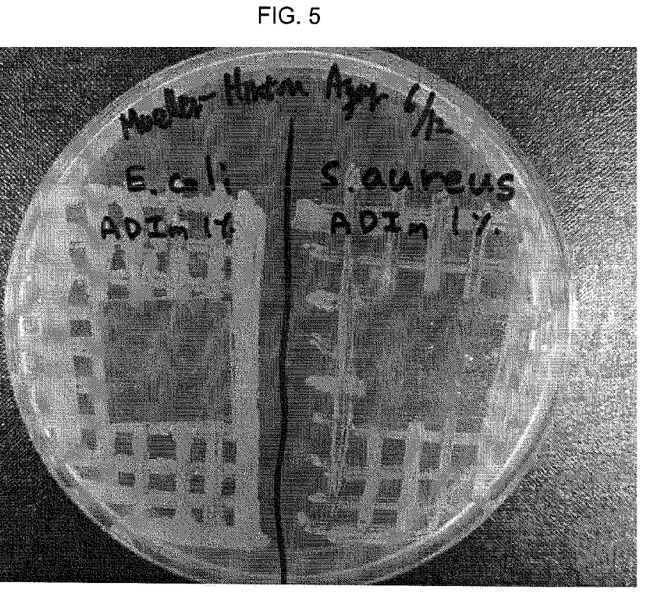
FIG. 5 is a photograph of antibacterial activity evaluation according to example 2-4.
Figure 6:
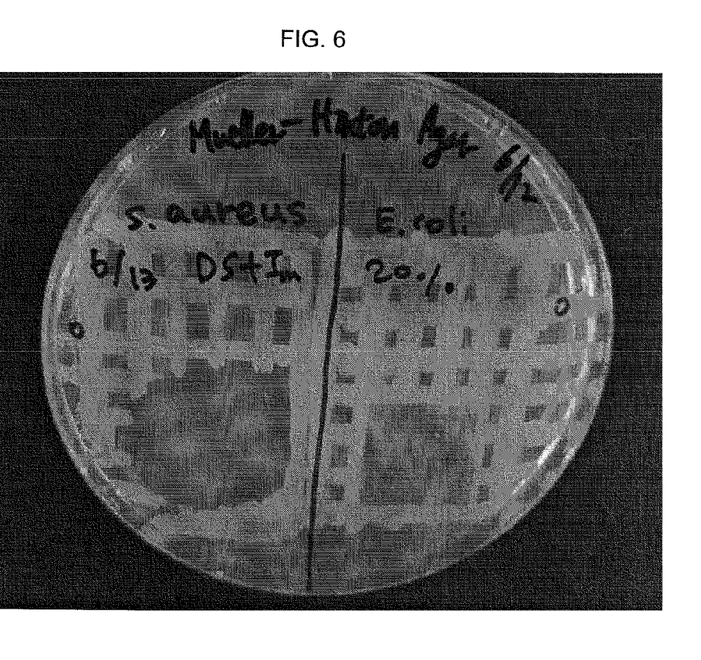
FIG. 6 is a photograph of antibacterial activity evaluation according to example 3-1.
Figure 7:
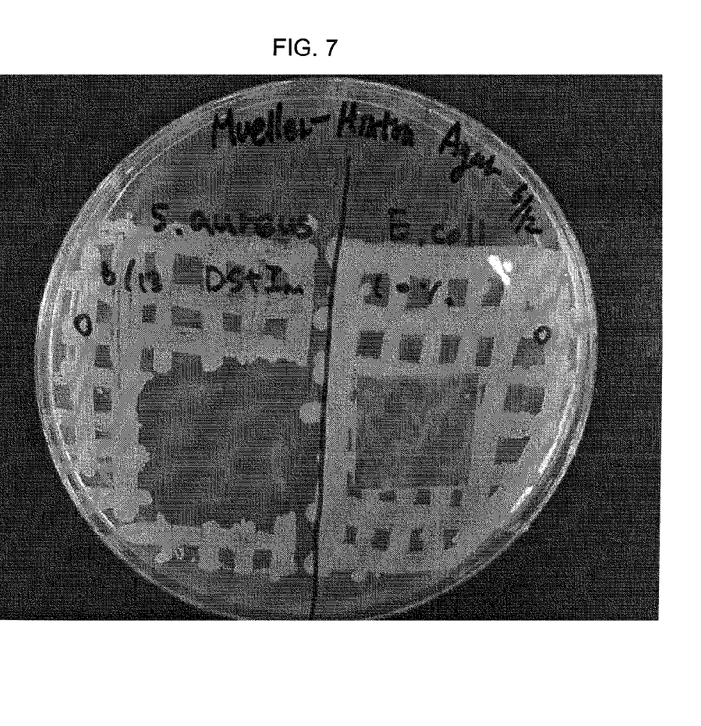
FIG. 7 is a photograph of antibacterial activity evaluation according to example 3-2.
Figure 8:
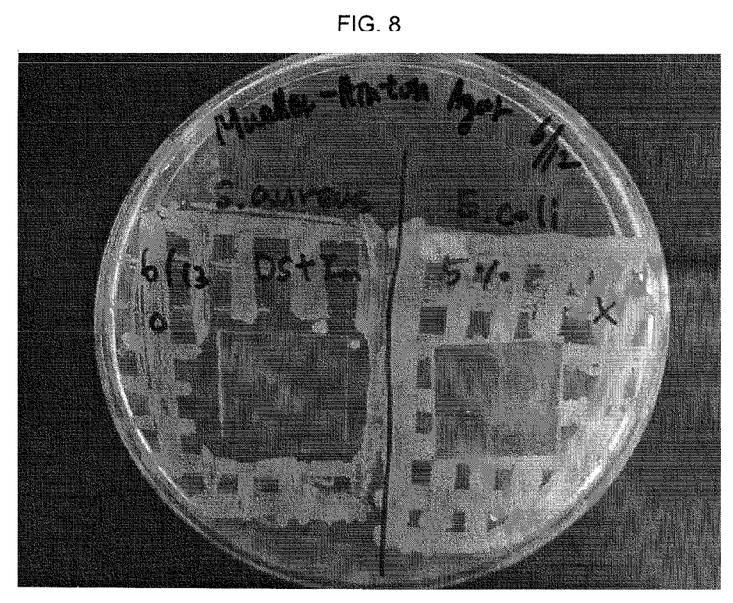
FIG. 8 is a photograph of antibacterial activity evaluation according to example 3-3.

| Sample name | Content | Colon bacillus (ATCC 103536) | Staphylococcus (ATCC65389) | Related drawing |
|---|---|---|---|---|
| Example 2-1 | ADIm 20 mol % | ○ | ○ | FIG. 2 |
| Example 2-2 | ADIm 10 mol % | ○ | ○ | FIG. 3 |
| Example 2-3 | ADIm 5 mol % | X | ○ | FIG. 4 |
| Example 2-4 | ADIm 1 mol % | X | ○ | FIG. 5 |
| Example 2-5 | ADIm 0.1 mol % | X | X | — |
| Example 3-1 | DStIm 20 mol % | ○ | ○ | FIG. 6 |
| Example 3-2 | DStIm 10 mol % | ○ | ○ | FIG. 7 |
| Example 3-3 | DStIm 5 mol % | X | ○ | FIG. 8 |

TABLE 6-continued

Evaluation of antibacterial activity

Figure 9:
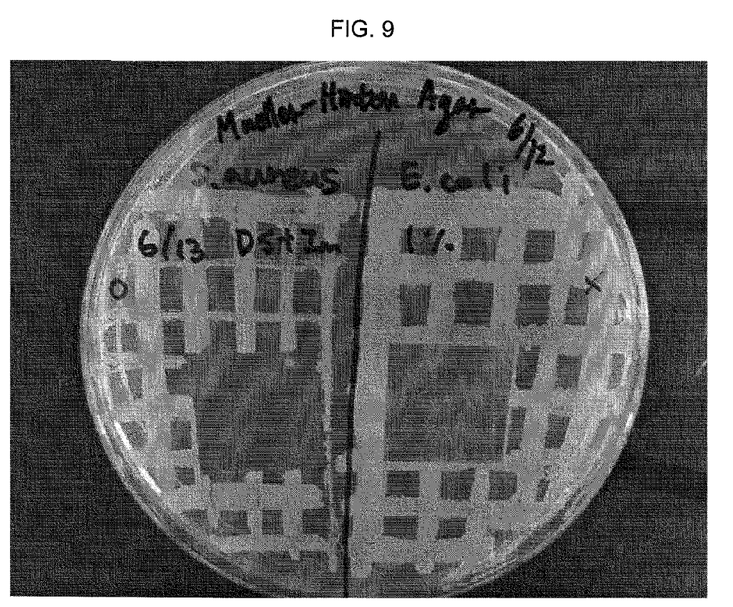
FIG. 9 is a photograph of antibacterial activity evaluation according to example 3-4.

| Sample name | Content | Colon bacillus (ATCC 103536) | Staphylococcus (ATCC65389) | Related drawing |
|---|---|---|---|---|
| Example 3-4 | DStIm 1 mol % | X | ○ | FIG. 9 |
| Example 3-5 | DStIm 0.1 mol % | X | X | — |

Note)
○ indicates that antibacterial activity noticeably appeared, and X indicates that antibacterial activity did not appear Also, results obtained by capturing the test results of the same sample are shown in FIG. 2. Referring to Table 6 and FIGS. 2 through 9, it was confirmed that photocurable film containing imidazolium prepared by irradiating light thereto by a conveyer belt has a noticeably high antibacterial activity over two types of bacterium. Photocurable film samples each containing 20, 10, 5, and 1 mol % of ADIm(Br) and DStIm (Cl) were evaluated to have very excellent antibacterial activity with respect to *staphylococcus*, and when the two types of imidazolium were contained by 20 and 10 mol %, antibacterial activity with respect to colon bacterium was evaluated to have excellent antibacterial activity. Namely, it was confirmed that the antibacterial imidazolium salt had excellent antibacterial activity for both the Gram positive *bacillus* and Gram negative *bacillus*.

EXAMPLE 8

Evaluation of Antibacterial Activity of Imidazolium Salt for Various Strains

MIC test results obtained by quantitatively measuring as to whether it had an antibacterial activity with respect to various strains, while adjusting concentration of ADIm(Br) are shown in Table 7.

TABLE 7

| ADIm(Br) concentration (μg/ml) | Strains having antibiosis |
|---|---|
| 1000 | ① *Staphylococcus aureus* (ATCC 65389) |
| | ② *Staphylococcus aureus* (ATCC 25923) |
| | ③ *Enterobacter cloacae* (ATCC 27508) |
| | ④ *Escherichia coli* (ATCC 10536) |
| | ⑤ *Escherichia coli* (ATCC 25922) |
| | ⑥ *Bacillus subtillis* (ATCC 6633) |
| | ⑦ *Bacillus cereus* (ATCC 27348) |
| | ⑧ *Salmonella typhimurium* (ATCC 1331) |
| | ⑨ *Moraxella catanhalis* (ATCC 25240) |
| | ⑩ *Serratia marcescens* (ATCC 27117) |
| | ⑪ *Proteus vulgaris* (ATCC 6059) |
| 500 | ① *Staphylococcus aureus* (ATCC 65389) |
| | ② *Staphylococcus aureus* (ATCC 25923) |
| | ③ *Enterobacter cloacae* (ATCC 27508) |
| | ④ *Escherichia coli* (ATCC 10536) |
| | ⑤ *Escherichia coli* (ATCC 25922) |
| | ⑥ *Bacillus subtillis* (ATCC 6633) |
| | ⑦ *Bacillus cereus* (ATCC 27348) |
| | ⑪ *Proteus vulgaris* (ATCC 6059) |
| 250 | ③ *Enterobacter cloacae* (ATCC 27508) |
| | ④ *Escherichia coli* (ATCC 10536) |
| | ⑤ *Escherichia coli* (ATCC 25922) |
| | ⑥ *Bacillus subtillis* (ATCC 6633) |
| | ⑦ *Bacillus cereus* (ATCC 27348) |
| 125 | ③ *Enterobacter cloacae* (ATCC 27508) |
| | ④ *Escherichia coli* (ATCC 10536) |
| | ⑦ *Bacillus cereus* (ATCC 27348) |
| 62.5 | ③ *Enterobacter cloacae* (ATCC 27508) |
| | ④ *Escherichia coli* (ATCC 10536) |

TABLE 7-continued

| ADIm(Br) concentration (μg/ml) | Strains having antibiosis |
|---|---|
| 31.25 | ③ *Enterobacter cloacae* (ATCC 27508) |
| | ④ *Escherichia coli* (ATCC 10536) |
| 15.625 | ④ *Escherichia coli* (ATCC 10536) |

Referring to the results of Table 7, ADIm(Br) has very excellent antibacterial activity, similar to that of benzoalconium chloride (BKC) currently used as a daily disinfectant commercially. So it is confirmed that ADIm(Br) has antibiosis over various strains. Also, the imidazolium salt had excellent activity to colon *bacillus* even at below 200 μg/ml. So it is confirmed that imidazolium salt had excellent antibacterial performance with respect to colon *bacillus* although a small amount thereof is applied.

Referring to the results of the examples, antibacterial activity test was performed on the photocurable film samples containing the imidazolium prepared in the present invention by AATCC TM147 and it was observed that *staphylococcus* and colon *bacillus* were not grown in the culture medium. Thus, it was confirmed that the photocurable film sample containing imidazolium salt in which a long alkyl group like dodecyl is substituted as prepared in the present invention has excellent antibacterial activity.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A photocurable coating composition comprising:
    20 to 50 mol % of thiol compound including 1 to 4 thiol groups;
    20 to 50 mol % of ene compound including carbon-carbon double bond;
    0.1 to 10 mol % of photoinitiator; and
    1.0 to 50 mol % of an antibacterial imidazolium compound represented by Chemical Formula 1 as follows:

[Chemical Formula 1]

wherein, $X^-$ is an anion selected from the group consisting of $Cl^-$, $Br^-$, $BF_4^-$, $PF_6^-$, $SbF_6^-$, $CF_3SO_3^-$, $(CF_3SO_3)_2N^-$, $ArSO_3^-$, $CF_3CO_2^-$, and $CH_3CO_2^-$, $R^1$ is an allyl group including a carbon-carbon double bond, and $R^2$ is a linear alkyl group represented by $(CH_2)_xY$, wherein x is an integer of 12 to 20, and Y is H.

2. The photocurable coating composition of claim 1, wherein the photocurable coating composition is liquid phase having viscosity ranging from 50 to 3000 cPs at 25° C.

3. The photocurable coating composition of claim 1, wherein the antibacterial imidazolium compound includes any one selected from the group consisting of 1-allyl-3-dodecylimidazolium salt, 1-dodecyl-3-4-vinylbenzyl)imidazolium salt, and a combination thereof.

4. The photocurable coating composition of claim 1, wherein a sulfur-carbon bond is formed during a photocuring process.

* * * * *